US012605127B2

(12) United States Patent
Naito et al.

(10) Patent No.: US 12,605,127 B2
(45) Date of Patent: Apr. 21, 2026

(54) RADIOGRAPHIC APPARATUS, RADIATION DETECTOR, AND CONTROL APPARATUS AND METHOD OF RADIOGRAPHIC APPARATUS

(71) Applicant: CANON KABUSHIKI KAISHA, Tokyo (JP)

(72) Inventors: Yuichi Naito, Kanagawa (JP); Akira Tsukuda, Tokyo (JP); Kai Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 254 days.

(21) Appl. No.: 18/515,018

(22) Filed: Nov. 20, 2023

(65) Prior Publication Data

US 2024/0081756 A1     Mar. 14, 2024

Related U.S. Application Data

(63) Continuation of application No. PCT/JP2022/020574, filed on May 17, 2022.

(30) Foreign Application Priority Data

May 27, 2021     (JP) ................................. 2021-089319

(51) Int. Cl.
| | |
|---|---|
| *A61B 6/08* | (2006.01) |
| *A61B 6/00* | (2024.01) |

(52) U.S. Cl.
CPC .............. *A61B 6/08* (2013.01); *A61B 6/4405* (2013.01); *A61B 6/548* (2013.01)

(58) Field of Classification Search
CPC ........... A61B 6/08; A61B 6/42; A61B 6/4405; A61B 6/464; A61B 6/547; A61B 6/548; A61B 6/587
See application file for complete search history.

(56) References Cited

U.S. PATENT DOCUMENTS

| | | | |
|---|---|---|---|
| 6,409,382 B1 * | 6/2002 | Akutsu | ................. A61B 6/467 378/114 |
| 7,748,900 B2 * | 7/2010 | Maschke | .............. A61B 6/4458 378/197 |

(Continued)

FOREIGN PATENT DOCUMENTS

| | | |
|---|---|---|
| JP | 2003310591 A | 11/2003 |
| JP | 2006158508 A | 6/2006 |

(Continued)

*Primary Examiner* — David J Makiya
*Assistant Examiner* — Soorena Kefayati
(74) *Attorney, Agent, or Firm* — Canon U.S.A., Inc. IP Division

(57)     ABSTRACT
A radiographic apparatus includes a radiation detector configured to perform radiographic imaging, an orientation measurement unit configured to perform measurement of orientation of the radiation detector, a signal output unit configured to output a trigger signal between reception of a stop signal indicating that a visiting cart carrying the radiation detector is at rest or stops and reception of a completion signal indicating completion of positioning of the radiation detector taken out of the visiting cart and a radiation generation apparatus for the radiographic imaging, the visiting cart being configured to carry the radiation generation apparatus and the radiation detector, and a control unit configured to control the orientation measurement unit to reduce a sampling period of the measurement based on reception of the trigger signal.

19 Claims, 9 Drawing Sheets

(56)             References Cited

U.S. PATENT DOCUMENTS

| | | | |
|---|---|---|---|
| 2012/0045037 A1* | 2/2012 | Carmichael | A61B 6/462 |
| | | | 378/198 |
| 2013/0170619 A1* | 7/2013 | Kamitake | A61B 6/00 |
| | | | 378/62 |
| 2015/0043712 A1* | 2/2015 | Wang | A61B 6/4021 |
| | | | 378/42 |
| 2015/0078527 A1* | 3/2015 | Iwamoto | A61B 6/4283 |
| | | | 378/91 |
| 2015/0078529 A1* | 3/2015 | Tsubota | A61B 6/4405 |
| | | | 378/91 |
| 2015/0201899 A1* | 7/2015 | Uchinomiya | A61B 6/547 |
| | | | 378/62 |
| 2016/0287193 A1* | 10/2016 | Katsumata | A61B 6/54 |
| 2017/0000429 A1* | 1/2017 | Nose | B60B 37/04 |
| 2017/0303885 A1* | 10/2017 | Hosoki | A61B 6/542 |
| 2018/0042097 A1* | 2/2018 | Kim | A61B 6/56 |
| 2019/0343592 A1* | 11/2019 | Elen | A61B 6/4405 |
| 2020/0107799 A1* | 4/2020 | Nebosis | A61B 6/587 |
| 2021/0077055 A1* | 3/2021 | Jun | A61B 6/56 |
| 2021/0089043 A1* | 3/2021 | Deinlein | G06N 20/00 |
| 2021/0345977 A1* | 11/2021 | Kumar | B60B 19/003 |

FOREIGN PATENT DOCUMENTS

| | | | |
|---|---|---|---|
| JP | 2015083113 A | 4/2015 |
| JP | 2015083114 A | 4/2015 |
| JP | 2017000233 A | 1/2017 |
| JP | 2018007923 A | 1/2018 |

* cited by examiner

FIG.1A
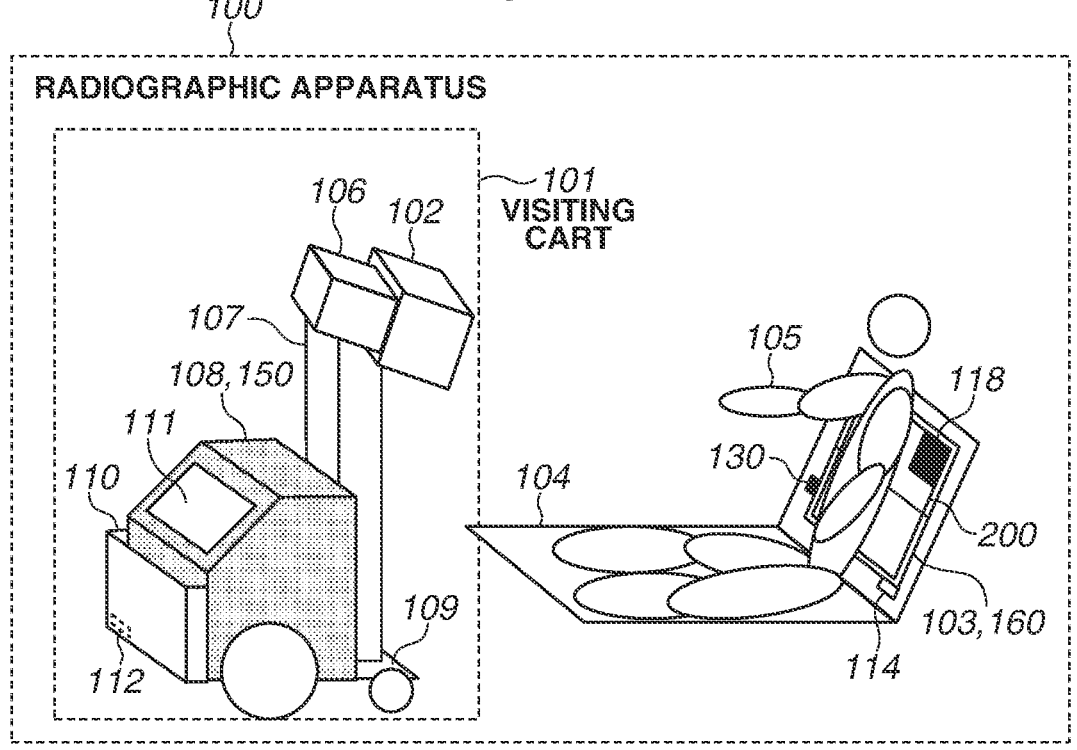
FIG.1B
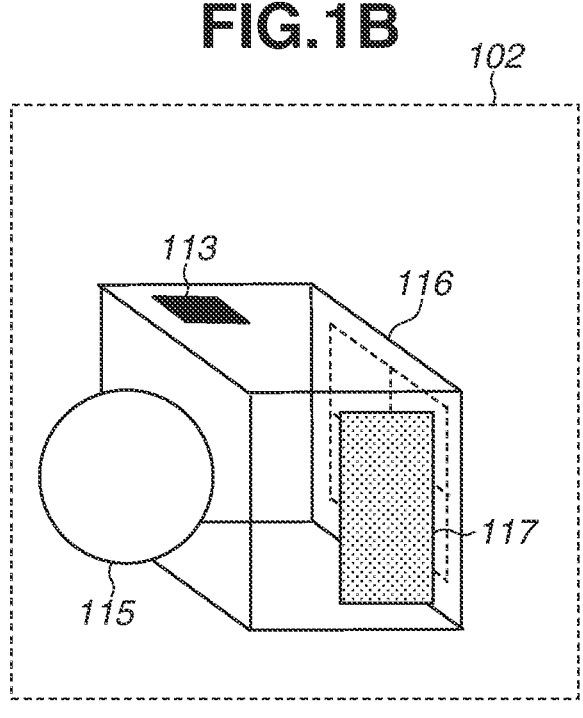

FIG.4

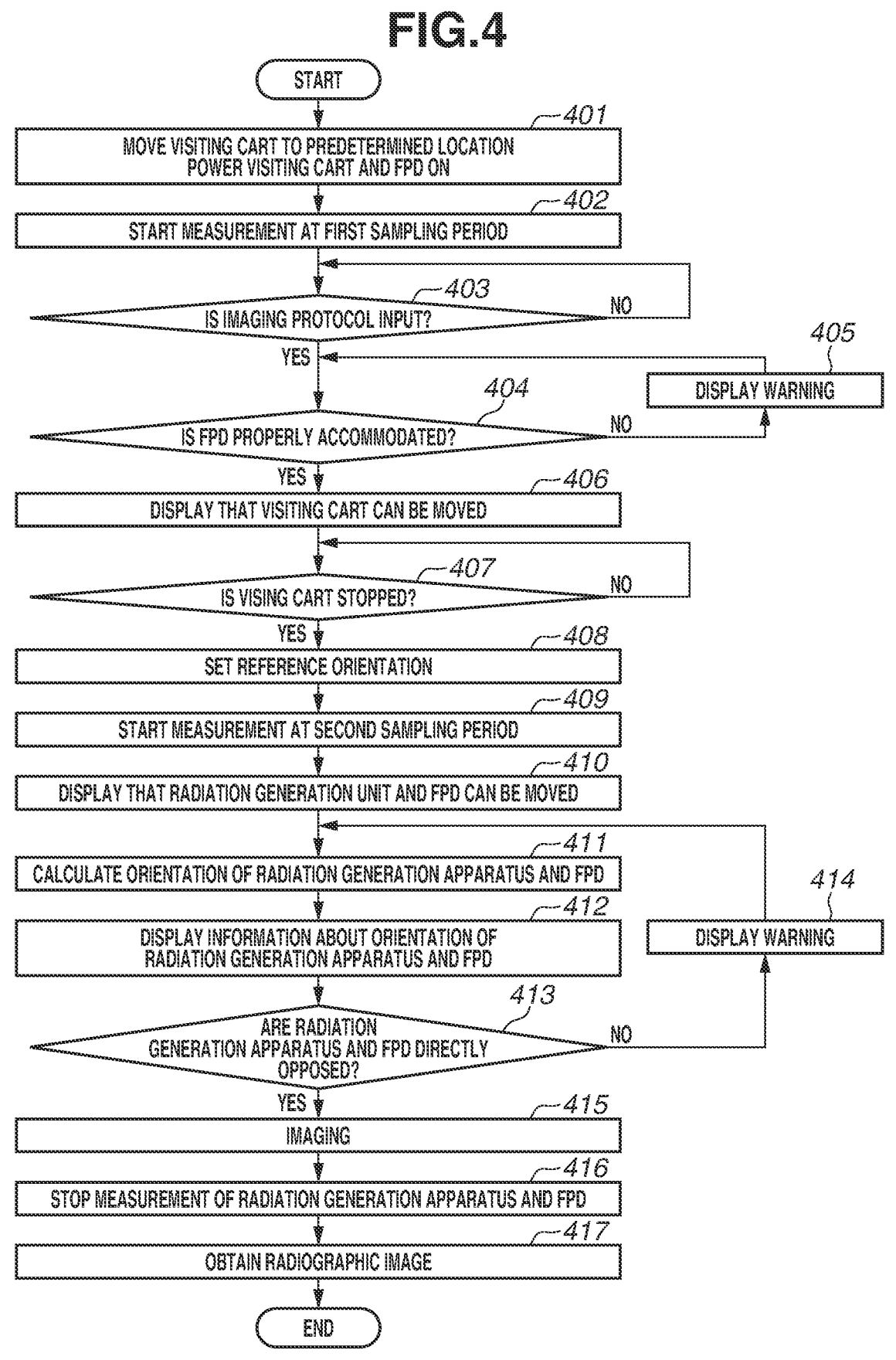

```
                        ( START )
                            │
                            ▼
    ┌──────────────────────────────────────────────────┐ ⌐401
    │ MOVE VISITING CART TO PREDETERMINED LOCATION       │
    │ POWER VISITING CART AND FPD ON                     │
    └──────────────────────────────────────────────────┘
                            │
                            ▼
    ┌──────────────────────────────────────────────────┐ ⌐402
    │ START MEASUREMENT AT FIRST SAMPLING PERIOD          │
    └──────────────────────────────────────────────────┘
                            │
                            ▼◄─────────────────────────┐
              ◄────────────────────────⌐403            │
            ◄       IS IMAGING PROTOCOL INPUT?    ►  NO─┘
                            │
                          YES ◄─────────────────────────┐
                            │                            │
                            ▼          ⌐404              │
            ◄       IS FPD PROPERLY ACCOMMODATED?  ►  NO─┤
                            │                            │
                          YES                            │  405
                            │           ┌─────────────────────────┐
                            ▼           │     DISPLAY WARNING      │
    ┌──────────────────────────────┐ ⌐406 └─────────────────────────┘
    │ DISPLAY THAT VISITING CART CAN BE MOVED            │
    └──────────────────────────────────────────────────┘
                            │
                            ▼◄─────────────────────────┐
              ◄────────────────────────⌐407            │
            ◄       IS VISING CART STOPPED?     ►    NO─┘
                            │
                          YES
                            ▼
    ┌──────────────────────────────────────────────────┐ ⌐408
    │ SET REFERENCE ORIENTATION                          │
    └──────────────────────────────────────────────────┘
                            │
                            ▼
    ┌──────────────────────────────────────────────────┐ ⌐409
    │ START MEASUREMENT AT SECOND SAMPLING PERIOD         │
    └──────────────────────────────────────────────────┘
                            │
                            ▼
    ┌──────────────────────────────────────────────────┐ ⌐410
    │ DISPLAY THAT RADIATION GENERATION UNIT AND FPD CAN BE MOVED │
    └──────────────────────────────────────────────────┘
                            │
                            ▼◄─────────────────────────┐
    ┌──────────────────────────────────────────────────┐ ⌐411
    │ CALCULATE ORIENTATION OF RADIATION GENERATION APPARATUS AND FPD │
    └──────────────────────────────────────────────────┘
                            │                            │
                            ▼          ⌐412              │  414
    ┌──────────────────────────────────────────────────┐ ┌─────────────────────────┐
    │ DISPLAY INFORMATION ABOUT ORIENTATION OF           │ │     DISPLAY WARNING      │
    │ RADIATION GENERATION APPARATUS AND FPD             │ └─────────────────────────┘
    └──────────────────────────────────────────────────┘
                            │           ⌐413
                            ▼
            ◄     ARE RADIATION                          
            ◄  GENERATION APPARATUS AND FPD DIRECTLY  ► NO─┘
                    OPPOSED?
                            │
                          YES
                            ▼
    ┌──────────────────────────────────────────────────┐ ⌐415
    │ IMAGING                                            │
    └──────────────────────────────────────────────────┘
                            │
                            ▼
    ┌──────────────────────────────────────────────────┐ ⌐416
    │ STOP MEASUREMENT OF RADIATION GENERATION APPARATUS AND FPD │
    └──────────────────────────────────────────────────┘
                            │
                            ▼
    ┌──────────────────────────────────────────────────┐ ⌐417
    │ OBTAIN RADIOGRAPHIC IMAGE                          │
    └──────────────────────────────────────────────────┘
                            │
                            ▼
                        ( END )
```

FIG.5A

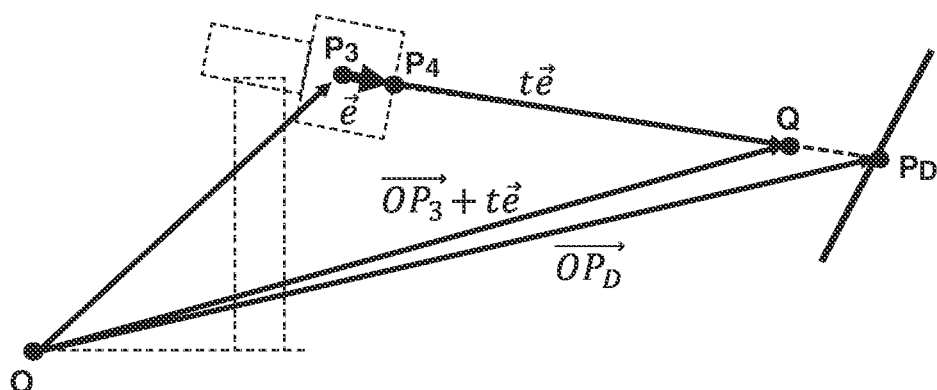

$$d_{min} = \min_{t \geq 0}\left|\overrightarrow{OP_D} - (\overrightarrow{OP_3} + t\vec{e})\right|$$

$0 \leq d_{min} \leq T_p$ ⟶ centers match $d_{min} > T$ or no solution ⟶ centers do not match

FIG.5B

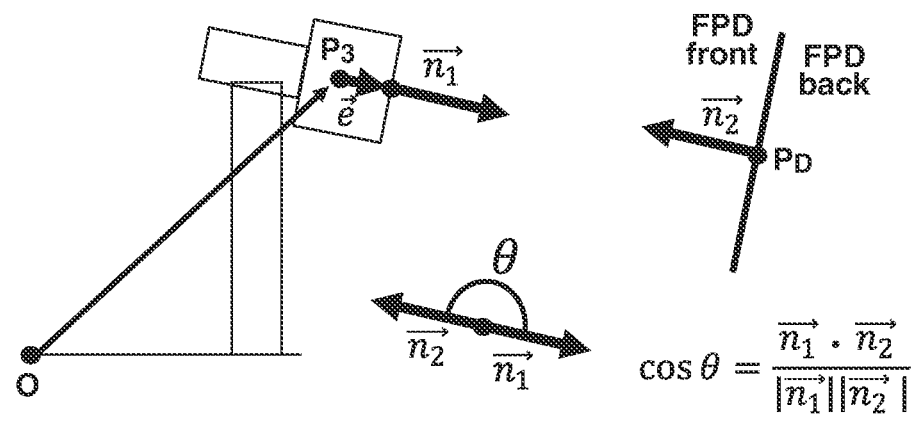

$$\cos\theta = \frac{\overrightarrow{n_1} \cdot \overrightarrow{n_2}}{|\overrightarrow{n_1}||\overrightarrow{n_2}|}$$

$\cos\theta \leq -1 + T_A$ ⟶ plane of irradiation field and incident surface are parallel otherwise ⟶ plane of irradiation field and incident plane are not parallel

MOVE TOWARD OBJECT

Z

PULL
FPD OUT

INSTALL FPD
BEHIND OBJECT

X

Y

TRASPORT FPD
WITH VISITING CART

SPEED
IN X-AXIS
DIRECTION

TIME t

SPEED
IN Z-AXIS
DIRECTION

TIME t

TS1

TS2

SAMPLING PERIOD

TIME t t100    t101 t102    t103 t104 t105

MOVE TOWARD OBJECT

PULL
FPD OUT

INSTALL FPD
BEHIND OBJECT

TRASPORT FPD
WITH VISITING CART

SPEED
IN X-AXIS
DIRECTION

TIME t

SPEED
IN Z-AXIS
DIRECTION

TIME t

TS1

TS2

SAMPLING PERIOD

TIME t t200      t201      t204    t205 t202      t206 t203

RADIOGRAPHIC APPARATUS, RADIATION DETECTOR, AND CONTROL APPARATUS AND METHOD OF RADIOGRAPHIC APPARATUS

CROSS-REFERENCE TO RELATED APPLICATIONS

This application is a Continuation of International Patent Application No. PCT/JP2022/020574, filed May 17, 2022, which claims the benefit of Japanese Patent Application No. 2021-089319, filed May 27, 2021, both of which are hereby incorporated by reference herein in their entirety.

BACKGROUND OF THE INVENTION

Field of the Invention

The present invention relates to a radiographic apparatus, a radiation detector, and control apparatus and method of the radiographic apparatus.

Background Art

Flat panel detectors (FPDs) made of semiconductor materials are now prevalent as radiation detectors for use in medical image diagnosis and nondestructive tests using radiation, such as X-rays. Radiographic apparatuses combining radiation detectors like these and radiation generation apparatuses for generating radiation are put to use.

As a function of such a radiographic apparatus, one for supporting positioning between the plane of the irradiation field of radiation emitted from the radiation generation apparatus and the incident surface of the radiation detector by calculating and displaying the orientation of the radiation generation apparatus and the radiation detector has been put to practical use.

In a method for calculating the orientation of the radiation generation apparatus and the radiation detector, the radiation generation apparatus and the radiation detector are each configured to include an acceleration sensor or gyro sensor. The orientation is calculated from acceleration that is the output value of the acceleration sensor or angular velocity that is the output value of the gyro sensor.

For example, if a gyro sensor is used, orientation is calculated by adding up (integrating) angular velocities measured in minute times using the gyro sensor. If an acceleration sensor is used, orientation is calculated by once integrating the acceleration measured using the acceleration sensor to calculate speed at a specific time, and further integrating the speed to calculate a displacement (position).

For example, Patent Literature 1 discusses a method for calculating the position and rotation angle of a radiation generation apparatus or a radiation detector using an orientation measurement unit, such as an acceleration sensor.

CITATION LIST

Patent Literature

PTL 1: Japanese Patent Laid-Open No. 2018-007923

In calculating the position and rotation angle using the orientation measurement unit discussed in Patent Literature 1, the power consumption of the orientation measurement unit increases if the sampling period of the orientation measurement unit is reduced for the purpose of accuracy. For example, if a visiting cart on which a radiation detector and a radiation generation apparatus are mounted is battery-powered, the increased power consumption shortens the interval of charging of the battery and lowers the work efficiency.

SUMMARY OF THE INVENTION

The present invention is directed to providing a radiographic apparatus that is capable of accurately calculating the orientations of a radiation generation apparatus and a radiation detector while reducing the power consumption of an orientation measurement unit for measuring the orientations of the radiation generation apparatus and the radiation detector.

According to an aspect of the present invention, a radiographic apparatus includes a radiation detector configured to perform radiographic imaging, an orientation measurement unit configured to perform measurement of orientation of the radiation detector, a signal output unit configured to output a trigger signal between reception of a stop signal indicating that a visiting cart carrying the radiation detector is at rest or stops and reception of a completion signal indicating completion of positioning of the radiation detector taken out of the visiting cart and a radiation generation apparatus for the radiographic imaging, the visiting cart being configured to carry the radiation generation apparatus and the radiation detector, and a control unit configured to control the orientation measurement unit to reduce a sampling period of the measurement based on reception of the trigger signal.

Further features of the present invention will become apparent from the following description of exemplary embodiments with reference to the attached drawings.

BRIEF DESCRIPTION OF THE DRAWINGS

FIGS. 1A and 1B are each a conceptual diagram illustrating a configuration example of a radiographic apparatus according to a first exemplary embodiment.

FIG. 4 is a flowchart illustrating an operation of the radiographic apparatus according to the first exemplary embodiment.

FIGS. 5A and 5B are each a diagram illustrating an example of a technique for checking a directly opposed relationship between the radiation generation apparatus and the radiation detector according to the first exemplary embodiment.

DESCRIPTION OF THE EMBODIMENTS

Figure 2:
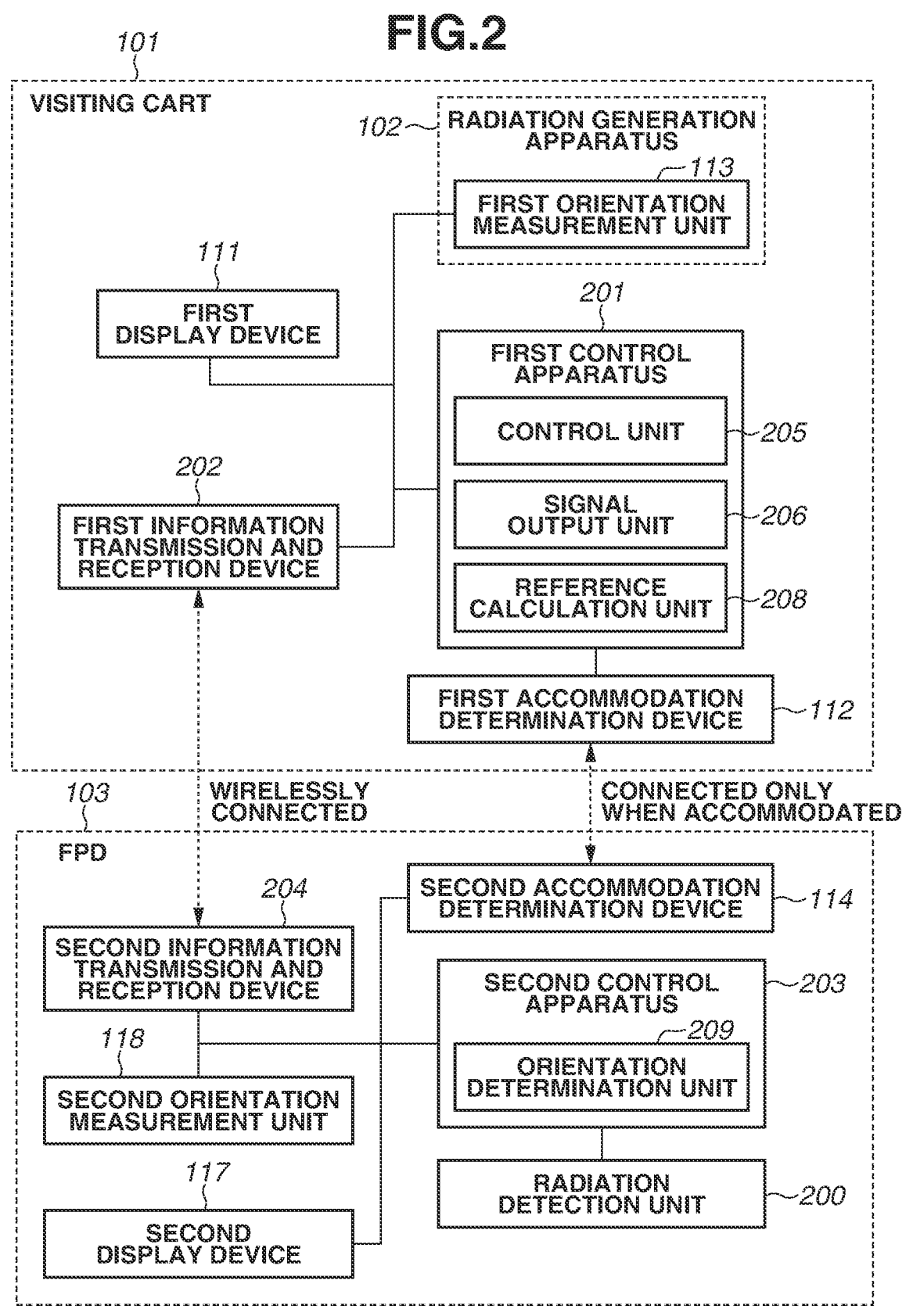
FIG. 2 is a block diagram illustrating a configuration example of a visiting cart and a radiation detector according to the first exemplary embodiment.

Exemplary embodiments of the present invention will be described below with reference to the attached drawings.

The following exemplary embodiments are not intended to limit the invention set forth in the claims. While a plurality of features is described in the exemplary embodiments, all the features are not necessarily essential to the invention, and more than one of the features may be combined in any given manner. In the attached drawings, the same or similar configurations are denoted by the same reference numerals. A redundant description thereof will be omitted. The term radiation refers typically to X-rays, whereas other radiations such as α-rays, β-rays, γ-rays, particle beams, and cosmic rays may be included.

FIG. 1A is a conceptual diagram illustrating a configuration example of a radiographic apparatus 100 according to a first exemplary embodiment of the present invention.

A visiting cart 101 is a movable cart including a moving mechanism, such as wheels. The visiting cart 101 is configured so that a radiation generation apparatus 102 is mountable thereon, and used to perform radiographic imaging with a flat panel detector (FPD; an example of a radiation detector) 103. The FPD 103 is installed behind an object 105 which is lies down on a bed 104 in performing radiographic imaging. The FPD 103 generates a radiation-based image of the object 105 based on radiation that is emitted from the radiation generation apparatus 102 and with which a radiation detection unit 200 is irradiated through the object 105.

The radiation detection unit 200 includes a scintillator for converting the irradiated radiation into light, and a pixel array including a two-dimensional array of photoelectric conversion elements for converting the light from the scintillator into electrical charges. A driving circuit (not illustrated) scans the pixel array, so that the radiation-based electrical charges generated by the radiation detection unit 200 are sequentially passed to a reading circuit (not illustrated) to generate a radiation-based image. The image generated by the radiation detection unit 200 is transmitted to a second control apparatus 203 to be described below. The second control apparatus 203 performs image processing as appropriate.

The visiting cart 101 includes a first arm 106 and a second arm 107 for supporting the radiation generation apparatus 102 so that the orientation of the radiation generation apparatus 102 is changeable. The visiting cart 101 also includes a housing 108, a pedestal 109, and an FPD accommodation unit 110.

In the present exemplary embodiment, the first arm 106 is connected to the radiation generation apparatus 102 and the second arm 107. The second arm 107 is connected to the first arm 106 and the pedestal 109. The housing 108 has a first display device 111 on its outside.

A battery 150 that supplies power for driving the visiting cart 101 is built in the housing 108, and the visiting cart 101 can be driven for a certain time without needing power supply via a cable. The housing 108 may include an electrical connector to power the battery 150 through connection with an external power supply. The battery 150 may be detachable from the housing 108 for power supply. The battery 150 also functions as a power supply unit capable of supplying power to a battery 160 of the FPD 103 via electrical connectors of a first accommodation determination device 112 and a second accommodation determination device 114 to be described below.

The housing 108 also includes a high voltage generation apparatus, a first control apparatus 201 to be described with reference to FIG. 2 (not illustrated in FIGS. 1A and 1B), and a first information transmission and reception device 202 (not illustrated in FIGS. 1A and 1B).

The FPD accommodation unit 110 is a pocket that the visiting cart 101 has so that the FPD 103 can be accommodated in the visiting cart 101. The FPD accommodation unit 110 includes the first accommodation determination device 112 for determining whether the FPD 103 is accommodated. For example, the first accommodation determination device 112 and the second accommodation determination device 114 to be described below are configured as a pair of electrically connectable connectors. The accommodation of the FPD 103 in the FPD accommodation unit 110 can be determined based on the connection of the connectors.

The first display device 111 includes a touchscreen and can receive user's input. As additional input devices for receiving the user's input, the visiting cart 101 may include a keyboard, a mouse, a voice recognition device, and/or a user orientation recognition device using a range sensor, for example.

The FPD 103 includes the built-in battery 160 that supplies power for driving the FPD 103. The FPD 103 can be driven for a certain time without needing power supply via a cable. The FPD 103 includes an electrical connector, and can power the battery 160 through connection with an external power supply. The battery 160 may be configured to be electrically connectable to the battery 150 of the visiting cart 101, to enable power supply. The battery 160 may be configured to be detachable from the FPD 103 so that the battery 160 can be powered by an external power supply.

The FPD 103 according to the present exemplary embodiment includes a second orientation measurement unit 118, the second accommodation determination device 114 that is an accommodation determination device included in the FPD 103, the second control apparatus 203 (not illustrated in FIGS. 1A and 1B), and a second information transmission and reception device 204 (not illustrated in FIGS. 1A and 1B). In the present exemplary embodiment, an acceleration sensor is used as the second orientation measurement unit 118. The second orientation measurement unit 118 may be an angular velocity sensor or a geomagnetic sensor. The FPD 103 further includes a switch 130 as an input unit for receiving the user's operation.

In FIG. 1A, the FPD 103 is arranged behind the object 105. In transporting the visiting cart 101 with the FPD 103, the FPD 103 is accommodated in the FPD accommodation unit 110 for transportation. When the user performs radiographic imaging, the FPD 103 accommodated in the FPD accommodation unit 110 is pulled out and installed behind the object 105.

FIG. 1B illustrates details of the radiation generation apparatus 102. The radiation generation apparatus 102 includes a tube 115 and a diaphragm 116. In the present exemplary embodiment, the diaphragm 116 includes a second display device 117 and a first orientation measurement unit 113. In the present exemplary embodiment, an acceleration sensor is used as the first orientation measurement unit 113. The first orientation measurement unit 113 may be an angular velocity sensor or a geomagnetic sensor.

The diaphragm 116 includes a mechanism that operates based on instructions from a computer mounted on the housing 108 to change the size of an irradiation field of radiation and a rotation angle of the radiation generation apparatus 102. Examples of the mechanism include a stepping motor.

As described above, the first accommodation determination device 112 and the second accommodation determination device 114 are configured as a pair of electrical connectors. For example, the first accommodation determination device 112 is disposed in the visiting cart 101, and the second accommodation determination device 114 on the FPD 103.

The pair of connectors constituting the first and second accommodation determination devices 112 and 114 may also have a function of charging the FPD 103 from the power supply unit included in the visiting cart 101 (i.e., battery 150). For example, when the connectors of the visiting cart 101 and the FPD 103 are connected and the FPD 103 is being charged, the FPD 103 can be determined to be accommodated in the FPD accommodation unit 110 of the visiting cart 101.

In the present exemplary embodiment, when the FPD 103 is accommodated, the visiting cart 101 and the FPD 103 are electrically connected via the first and second accommodation determination devices 112 and 114. However, the two accommodation determination devices do not necessarily need to be electrically connected for accommodation determination, since the purpose of the first and second determination accommodation devices 112 and 114 in the present exemplary embodiment is to obtain information indicating that the FPD 103 is at a specific location.

As an example, the functions of the first and second accommodation determination devices 112 and 114 may be implemented by devices supporting Bluetooth® or near-field communication (NFC), or other proximity determination devices.

As another example, a weight scale for measuring the weight of the FPD 103 may be attached to the FPD accommodation unit 110 of the visiting cart 101. In such a case, the accommodation of the FPD 103 in the FPD accommodation unit 110 can be determined based on the value of the weight scale. Here, if the FPD 103 has a rectangular imaging surface and its direction is desirably identified, the direction is determined by using a gravity sensor included in the FPD 103, for example.

The visiting cart 101 may include a camera, and the accommodation of the FPD 103 in the FPD accommodation unit 110 may be determined based on an image.

The FPD 103 may include a sensor for determining accommodation. For example, the FPD 103 may include sensors for detecting brightness at four corners. The FPD 103 can be determined to be accommodated in the FPD accommodation unit 110 if specific two of the sensors detect a high level of light and specific two detect a low level of light. This implementation can also determine the direction of accommodation.

If the second control apparatus 203 of the FPD 103 is configured to have the function of a control unit 205 to be described below, the accommodation determination can be performed by the FPD 103 alone. This can facilitate the implementation of the visiting cart 101.

FIG. 2 is a block diagram illustrating a configuration example of the visiting cart 101 and the FPD 103 according to the present exemplary embodiment.

The first control apparatus 201 is built in the visiting cart 101. The first control apparatus 201 may be a general-purpose computer constituted by hardware devices including a central processing unit (CPU), a main storage device, such as a dynamic random access memory (DRAM), and an auxiliary storage device, such as a solid-state drive (SSD) and a hard disk drive (HDD). The first control apparatus 201 has the functions of the control unit 205, a signal output unit 206, and a reference calculation unit 208 to be described below.

The first control apparatus 201 is connected to the radiation generation apparatus 102 and performs radiation-related control, such as exposure permission control. To calculate reference orientation of the radiation generation apparatus 102, the first control apparatus 201 is connected to the first orientation measurement unit 113. The reference calculation unit 208 included in the first control apparatus 201 can calculate the reference orientation of the radiation generation apparatus 102 from values measured by the first orientation measurement unit 113.

To calculate reference orientation of the FPD 103, the first connection apparatus 201 is connected to the second orientation measurement unit 118 via the first and second information transmission and reception devices 202 and 204. The reference calculation unit 208 can calculate the reference orientation of the FPD 103 from values measured by the second orientation measurement unit 118.

The control unit 205 sets the reference orientation of the radiation generation apparatus 102 and the FPD 103. The reference orientation is orientation serving as a reference at a point in time to calculate the orientation of an apparatus based on the values of an acceleration sensor. To calculate orientation using an acceleration sensor, the acceleration measured using the acceleration sensor is once integrated to calculate speed at a specific time, and the speed is then integrated again and converted into a displacement (position), which is added to the reference orientation. In the present exemplary embodiment, acceleration sensors are used as the first and second orientation measurement units 113 and 118.

The first control apparatus 201 is connected to the first information transmission and reception device 202. Examples of the first information transmission and reception device 202 include a wireless local area network (LAN) device, a Bluetooth® device, and an ultra-wideband (UWB) device. Using the first information transmission and reception device 202, the first control apparatus 201 can connect to the second information transmission and reception device 204 included in the FPD 103 and transmit and receive information to/from the FPD 103.

For example, in the present exemplary embodiment, the control unit 205 is disposed on the visiting cart 101, and information about the reference orientation of the FPD 103 is thus transmitted to the FPD 103 using the first and second information transmission and reception devices 202 and 204. The first and second information transmission and reception devices 202 and 204 also have the role of delivering information determined by an orientation determination unit 209 of the FPD 103 to the first control apparatus 201.

The first and second information transmission and reception devices 202 and 204 can further be used to exchange information about radiation control such as exposure permission control, and transmit an image obtained by the FPD 103 to the visiting cart 101. The first and second information transmission and reception devices 202 and 204 can also be used for the control unit 205 to transmit instructions about a measurement sampling period to the second orientation measurement unit 118. In the present exemplary embodiment, the first and second information transmission and reception devices 202 and 204 are wirelessly connected. However, the first and second information transmission and reception devices 202 and 204 may be connected in a wired manner.

The first display device 111 includes an input unit and is connected to the first control apparatus 201. The user can input an imaging protocol of radiographic imaging from the first display device 111. The input of the imaging protocol is detected by the first control apparatus 201.

The FPD 103 includes the second control apparatus 203, the second information transmission and reception device 204, the second orientation measurement unit 118, and the second accommodation determination device 114. The second control apparatus 203 has the function of the orientation determination unit 209 to determine whether the radiation generation apparatus 102 and the FPD 103 are directly opposed. As with the first control apparatus 201, the second control apparatus 203 can include a CPU, a main storage device, and an auxiliary storage device.

The second control apparatus 203 is desirably simple compared to the first control apparatus 201 on the visiting cart 101, since the FPD 103 is desirably small in size, light in weight, and low in power consumption. To achieve this, the second control apparatus 203 included in the FPD 103 may be a field-programmable gate array (FPGA) or a dedicated integrated circuit (IC) circuit.

To determine whether the radiation generation apparatus 102 and the FPD 103 are directly opposed, the orientation determination unit 209 calculates the orientation of the FPD 103 from the reference orientation that is calculated by the reference calculation unit 208 and set by the control unit 205 and the values that are measured by the second orientation measurement unit 118.

A rotation angle and an angular velocity about an X-axis at time t will be denoted by $\theta(t)$ and $\omega_\theta(t)$, a rotation angle and an angular velocity about a Y-axis by $\varphi(t)$ and $\omega_\varphi(t)$, a rotation angle and an angular velocity about a Z-axis by $\eta(t)$ and $\omega_\eta(t)$, a measurement interval of the angular velocities by $\Delta t$, and the number of measurements by n (here, $t=n\Delta t$ holds). Here, $\theta(t)$, $\varphi(t)$, and $\eta(t)$ are given by:

$$\theta(t) = \theta(0) + \sum_{k=1}^{n} \omega_\theta(k\Delta t)\Delta t, \qquad \text{Eq. 1}$$

$$\varphi(t) = \varphi(0) + \sum_{k=1}^{n} \omega_\varphi(k\Delta t)\Delta t, \text{ and} \qquad \text{Eq. 2}$$

$$\eta(t) = \eta(0) + \sum_{k=1}^{n} \omega_\eta(k\Delta t)\Delta t. \qquad \text{Eq. 3}$$

If a gyro sensor is mounted as the second orientation measurement unit 118, angular velocity values in the coordinate system of the gyro sensor can be obtained. In calculating an angle from an angular velocity measured using the gyro sensor, the angular velocity in the coordinate system of the gyro sensor is converted into one in a desired coordinate system. Known methods can be used for the conversion.

A position is derived by once calculating the sum of accelerations to derive a speed and then calculating the sum of speeds. The X-axis components of position, speed, and acceleration at time t will be denoted by $x(t)$, $v_x(t)$, and $a_x(t)$, the Y-axis components by $y(t)$, $v_y(t)$, and $a_y(t)$, and the Z-axis components by $z(t)$, $v_z(t)$, and $a_z(t)$. As with the angular velocities, the measurement interval is denoted by $\Delta t$, and the number of measurements by n (here, $t=n\Delta t$ holds). The speeds at time t are calculated by:

$$v_x(t) = v_x(0) + \sum_{k=1}^{n} a_x(k\Delta t)\Delta t, \qquad \text{Eq. 4}$$

$$v_y(t) = v_y(0) + \sum_{k=1}^{n} a_y(k\Delta t)\Delta t, \text{ and} \qquad \overline{\text{Eq. 5}}$$

-continued $$v_z(t) = v_z(0) + \sum_{k=1}^{n} a_z(k\Delta t)\Delta t. \qquad \text{Eq. 6}$$

The positions are thus given by:

$$x(t) = x(0) + \sum_{k=1}^{n} v_x(k\Delta t)\Delta t, \qquad \text{Eq. 7}$$

$$y(t) = y(0) + \sum_{k=1}^{n} v_y(k\Delta t)\Delta t, \text{ and} \qquad \text{Eq. 8}$$

$$z(t) = z(0) + \sum_{k=1}^{n} v_z(k\Delta t)\Delta t. \qquad \text{Eq. 9}$$

In the foregoing Eqs. 1 to 9, known numerical integration techniques, such as the trapezoidal rule and Simplon's rule, may be applied to improve the accuracy of the summation. The accelerations $a_x(t)$, $a_y(t)$, and $a_z(t)$ detected by the acceleration sensor include gravitational components. The direction of the gravity acting on the FPD 103 may be calculated using the angles $\theta(t)$, $\varphi(t)$, and $\eta(t)$ measured by the gyro sensor, for example, and the X, Y, and Z components of the gravitational acceleration may be subtracted from the accelerations.

Figure 3A:
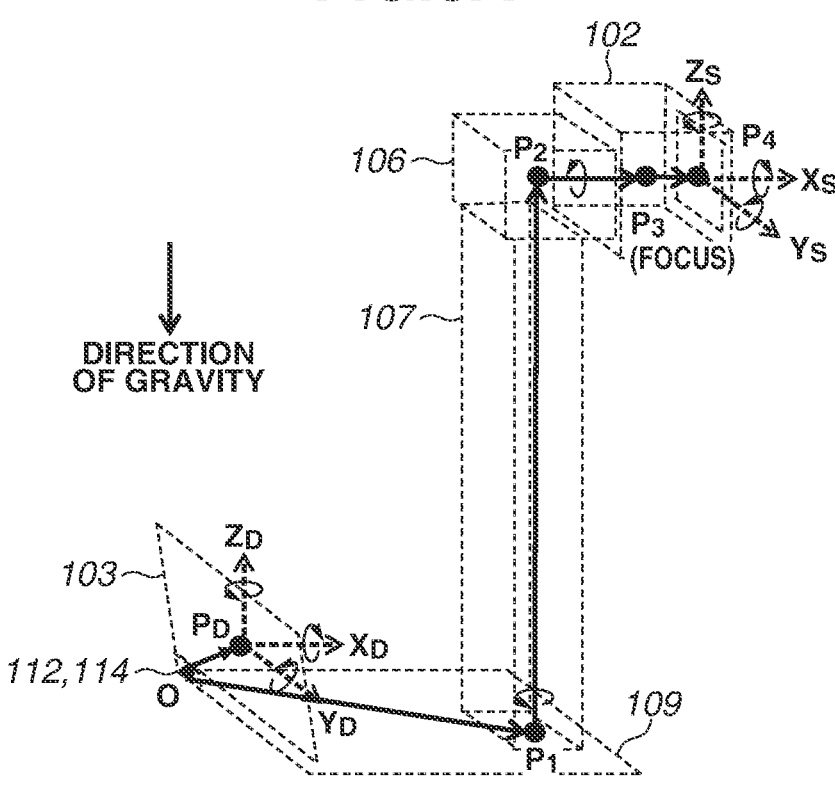
FIGS. 3A to 3C are each a diagram illustrating a relationship between the coordinates of the radiation detector and the coordinates of a radiation generation apparatus according to the first exemplary embodiment.
Figure 3B:
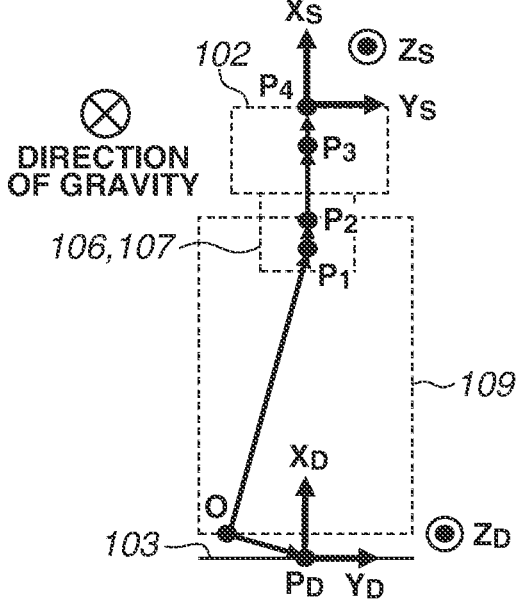
Figure 3C:
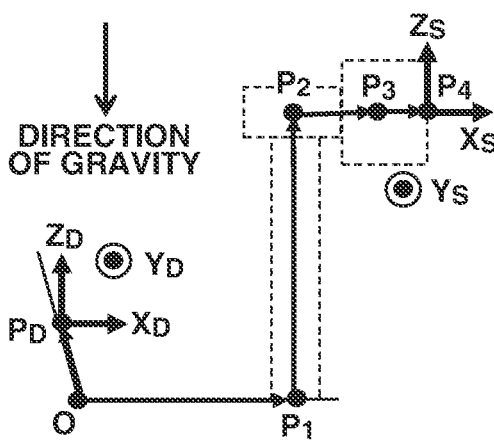

FIGS. 3A to 3C illustrate a coordinate relationship between coordinates $X_D$, $Y_D$, and $Z_D$ of the FPD 103 and coordinates $X_S$, $Y_S$, and $Z_S$ of the radiation generation apparatus 102 according to the present exemplary embodiment.

The coordinates of the FPD 103 and the coordinates of the radiation generation apparatus 102 are both determined to be relative coordinates from a reference point O. In the present exemplary embodiment, the reference point O is defined as a point at a location where the first and second accommodation determination devices 112 and 114 are connected. For example, a point, such as a corner or barycenter, of the area where the first and second accommodation determination devices 112 and 114 are connected is defined as the reference point O.

The coordinates of the FPD 103 are defined with reference to the center (e.g., barycenter) $P_D$ of the FPD 103, with a direction parallel with and reverse to the gravity as a Z-axis and with a horizontal plane (plane perpendicular to the acting direction of the gravity) as an XY plane. A Y direction is set to be parallel with the pedestal 109, and an X direction is defined to be perpendicular to the Y direction (within the XY plane).

The coordinates of the radiation generation apparatus 102 are similarly defined with respect to a center $P_4$ of the surface from which radiation is emitted, with a direction parallel with and reverse to the gravity as a Z-axis and with a horizontal plane (plane perpendicular to the acting direction of the gravity) as an XY plane. A Y direction is assumed to be parallel with the pedestal 109, and an X direction is defined to be perpendicular to the Y direction. If a source image receptor distance (SID; here, referring to the distance from the focus to the incident surface of the FPD 103) is calculated, a focus position $P_3$ of the tube 115 is used instead of $P_4$.

Here, the coordinates of the FPD 103 are expressed by a vector $OP_D$. The orientation of the FPD 103 is defined by rotations about the respective axes $X_D$, $Y_D$, and $Z_D$. If the FPD 103 is determined to be accommodated in the FPD accommodation unit 110 of the visiting cart 101, the orientation of the FPD 103 is determined by only the geometric layout of the FPD 103 and the FPD accommodation unit 110 during accommodation.

More specifically, when the FPD 103 is accommodated in the FPD accommodation unit 110 and connected by the first and second accommodation determination devices 112 and 114, the vector $OP_D$ indicating the orientation and the rotation angles about the axes $X_D$, $Y_D$, and $Z_D$ have values depending only on the external shapes of the members. The reference orientation of the FPD 103 may therefore refer to the vector $OP_D$ and the rotation angles about the axes $X_D$, $Y_D$, and $Z_D$ during accommodation.

Similarly, the coordinates of the radiation generation apparatus 102 are expressed by a vector $OP_4$. The vector $OP_4$ is expressed by the sum of four vectors $OP_1$, $P_1P_2$, $P_2P_3$, and $P_3P_4$.

The vector $OP_1$ is a vector from the reference point O to one end of the second arm 107. The vector $P_1P_2$ is a vector from the one end of the second arm 107 to the other end of the second arm 107 (in contact with the first arm 106). The vector $P_2P_3$ is a vector from one end of the first arm 106 to the focus of the tube 115. The vector $P_3P_4$ is a vector from the focus of the tube 115 to the center $P_4$ of the surface of the diaphragm 116 from which the radiation is emitted. The vector $OP_4$ is thus expressed as:

$$\overrightarrow{OP_4} = \overrightarrow{OP_1} + \overrightarrow{P_1P_2} + \overrightarrow{P_2P_3} + \overrightarrow{P_3P_4} \qquad \text{Eq. 10}$$

The coordinates of the focus are expressed as:

$$\overrightarrow{OP_3} = \overrightarrow{OP_1} + \overrightarrow{P_1P_2} + \overrightarrow{P_2P_3} \qquad \text{Eq. 11}$$

Of these vectors, the vector $OP_1$ is determined by the dimensions of the pedestal 109. The vector $P_1P_2$ is determined by the length (degree of extension and contraction) and rotation of the second arm 107. The vector $P_2P_3$ is determined by the length (degree of extension and contraction) and rotation of the first arm 106. The vector $P_3P_4$ is fixed (depends on the layout of the focus of the tube 115 and the dimensions of the diaphragm 116).

In other words, in the present exemplary embodiment, the quantities of the vector $OP_4$ to vary during actual use by the user are the length (degree of extension and contraction), direction, and rotation of the first arm 106, and the length, direction, and rotation of the second arm 107. The initial state of the radiation generation apparatus 102 can be calculated from such pieces of information.

In transporting the visiting cart 101, the first and second arms 106 and 107 are contracted as much as possible for easy transportation. In other words, during transportation of the visiting cart 101, the arms can be considered to be in a specific state. This state can be regarded as the reference state of the arms.

Whether the arms are in the reference state can be measured by using known configurations. For example, the directions and rotations can be measured using potentiometers at the respective contact points. The state of extension and contraction of each arm can be obtained using a distance meter. The arms may include mechanical or electrical switches that react only when the axes of the arms are in the reference state.

In the present exemplary embodiment, the rotation of the radiation generation apparatus 102 about the coordinates Xs, Ys, and Zs is calculated from the orientation of the first arm 106 and the orientation of the second arm 107. As described above, the first arm 106 can be controlled in terms of the direction and magnitude of the vector $P_2P_3$ as well as the rotation about the vector $P_2P_3$. The second arm 107 can be controlled in terms of the direction and magnitude of the vector $P_1P_2$ as well as the rotation about the vector $P_1P_2$. The rotation about the coordinates Xs, Ys, and Zs can be controlled by changing the directions, sizes, and rotations of the arms.

FIG. 4 is an operation flowchart of the radiographic apparatus 100 according to the first exemplary embodiment of the present invention.

In step 401, the user accommodates the FPD 103 into the FPD accommodation unit 110 of the visiting cart 101 and moves the visiting cart 101 to a predetermined location for imaging. Examples of the predetermined location include near the bed 104 where the object 105 lies. The user then powers the visiting cart 101 and the FPD 103 on. The processing proceeds to step 402.

In step 402, the control unit 205 sets the sampling periods at which the first and second orientation measurement units 113 and 118 measure values to a first sampling period TS1. With the setting completed, the first and second orientation measurement units 113 and 118 start measurement.

For example, the first sampling period TS1 is set to 1 sec. The first and second orientation measurement units 113 and 118 then perform measurement at intervals of 1 sec. To determine whether the radiation generation apparatus 102 and the FPD 103 are directly opposed, the orientation determination unit 209 calculates the orientation of the radiation generation apparatus 102 and the FPD 103 based on the measured values. The processing proceeds to step 403.

In step 403, the user inputs an imaging protocol of radiographic imaging to the visiting cart 101. The imaging protocol is input via the display device 111 serving also as an input device, and the first control apparatus 201 detects the input. The imaging protocol may be input before a start of the round, specifically, before step 401. If the input of the imaging protocol is detected (YES in step 403), the processing proceeds to step 404. If the input of the imaging protocol is not detected (NO in step 403), the processing returns to step 403. In other words, step 403 is a step to wait until the user selects an imaging protocol.

In step 404, the control unit 205 determines whether the FPD 103 is accommodated in the FPD accommodation unit 110 of the visiting cart 101, using the first accommodation determination device 112 of the visiting cart 101 and the second accommodation determination device 114 of the FPD 103. If the FPD 103 is not properly accommodated (NO in step 404), the processing proceeds to step 405. In step 405, a warning is displayed since the reference orientation is unable to be correctly calculated. The processing then returns to step 404 to make the accommodation determination again. If the FPD 103 is determined to be properly accommodated (YES in step 404), the processing proceeds to step 406.

In step 406, the control unit 205 displays that the visiting cart 101 is movable on the first display device 111 to permit the user to move the visiting cart 101 for position adjustment. In response to the display, the user starts to move the visiting cart 101. The processing proceeds to step 407.

In the present exemplary embodiment, the movement of the visiting cart 101 is measured at the first sampling period TS1 by using the second orientation measurement unit 118 of the FPD 103 accommodated in the visiting cart 101. The movement of the visiting cart 101 may be measured by using the first orientation measurement unit 113 on the visiting cart 101. An additional orientation measurement unit, such as an acceleration sensor and a gyro sensor, may be mounted on the visiting cart 101 to provide the function.

In step 407, the first control apparatus 201 monitors the movement of the visiting cart 101 from the measurements of the second orientation measurement unit 118, and determines whether the visiting cart 101 is stopped. Step 407 is repeated until the visiting cart 101 is determined to be stopped. If the visiting cart 101 is stopped (YES in step 407), the processing proceeds to step 408.

The control unit 205 detects the stop of the visiting cart 101 from the speed measured by the second orientation measurement unit 118 of the FPD 103 on the visiting cart 101 or the additionally mounted orientation measurement unit. The control unit 205 outputs a stop signal as soon as the stop of the visiting cart 101 is detected.

If the speed is used for stop detection, a threshold may be set to determine that speed up to a predetermined value is zero in view of a noise component of the second orientation measurement unit 118 and/or the additionally installed orientation measurement unit. In other words, the control unit 205 detects the stop of the visiting cart 101 based on a comparison between the measured speed and the threshold.

If the visiting cart 101 has brakes, the control unit 205 may detect the stop of the visiting cart 101 based on a signal for detecting that the brakes are applied for a predetermined period.

If the visiting cart 101 is not moved for position adjustment, steps 406 and 407 may be omitted. In such a case, the determination to advance the processing to step 408 may be made if the movement of the visiting cart 101 is not detected for a certain time after the display of movability in step 406, for example. The determination may be made by the user making an input to not move the visiting cart 101 during the display of movability in step 406, using the function of the first display device 111 to receive user input.

In step 408, the control unit 205 calculates the orientation of the radiation generation apparatus 102 and the FPD 103 based on the values measured by using the first and second orientation measurement units 113 and 118, and sets the calculated orientation as the reference orientation. The processing proceeds to step 409.

In step 409, the signal output unit 206 outputs a trigger signal in response to the setting of the reference orientation. The trigger signal is used for issuing instructions about the timing to change the sampling periods of the first and second orientation measurement units 113 and 118. Receiving the trigger signal, the control unit 205 sets the sampling periods of the first and second orientation measurement units 113 and 118 to a second sampling period TS2 shorter than the first sampling period TS1. With the setting completed, the first and second orientation measurement units 113 and 118 start measurement at the second sampling period TS2.

For example, the second sampling period TS2 is set to 0.1 sec. Reducing the sampling periods of the first and second orientation measurement units 113 and 118 enables acquisition of accurate values, and the orientation of the radiation generation apparatus 102 and the FPD 103 can be calculated with high accuracy. The processing proceeds to step 410.

In step 410, the display device 111 displays to the user that the radiation generation apparatus 102 and the FPD 103 is able to be positioned, specifically, the radiation generation apparatus 102 and the FPD 103 is movable for radiographic imaging. In response to the display, the user starts to move the radiation generation apparatus 102 and the FPD 103. The processing proceeds to step 411.

In step 411, the orientation determination unit 209 calculates the orientation of the radiation generation apparatus 102 and the FPD 103 based on the values of the first and second orientation measurement units 113 and 118 obtained at the second sampling period TS2. Here, the X, Y, and Z, three components of the angle and the X, Y, and Z, three components of the position (distance between the tube 115 and the image reception surface, i.e., SID) are calculated. The orientation of the radiation generation apparatus 102 and the FPD 103 can be determined from the reference orientation determined in step 409, using Eqs. 1 to 9.

The value of the SID can be calculated by:

$$|\overrightarrow{P_3 P_D}| =$$

$$|\overrightarrow{OP_D} - \overrightarrow{OP_3}| = \sqrt{\left(\overrightarrow{OP_D} - \overrightarrow{OP_3}\right)_x^2 + \left(\overrightarrow{OP_D} - \overrightarrow{OP_3}\right)_y^2 + \left(\overrightarrow{OP_D} - \overrightarrow{OP_3}\right)_z^2},$$

Eq. 12 where the vector $OP_D$ represents the center of the FPD 103 seen from the origin, the vector $OP_3$ represents the focus seen from the origin, the vector $P_3P_D$ is a vector from the focus to the center of the FPD 103, and the length of the vector $P_3P_D$ is the SID. In Eq. 12, ( )$_x$ expresses the magnitude of the X component of the vector. The same applies to the Y and Z components. The processing proceeds to step 412.

In step 412, the control unit 205 displays information about the calculated orientation of the radiation generation apparatus 102 and the FPD 103 on the first display device 111. This orientation information may be displayed on the second display device 117 of the FPD 103.

The user can check the displayed orientation information to see whether the current relationship in orientation between the radiation generation apparatus 102 and the FPD 103 is as intended by the user. The processing proceeds to step 413.

In step 413, the orientation determination unit 209 determines whether the radiation generation apparatus 102 and the FPD 103 are directly opposed from the relative relationship in orientation between the radiation generation apparatus 102 and the FPD 103. FIGS. 5A and 5B illustrate examples of techniques for checking the directly opposed relationship between the radiation generation apparatus 102 and the FPD 103. Referring to FIGS. 5A and 5B, how to determine whether the centers of the FPD 103 and the irradiation field of radiation match (FIG. 5A) and how to check whether the plane of the irradiation field and the incident surface of the FPD 103 are parallel (FIG. 5B) for the sake of checking that the radiation generation apparatus 102 and the FPD 103 are directly opposed will be described.

FIG. 5A illustrates a method for determining whether the centers of the FPD 103 and the irradiation field of radiation match. FIG. 5B illustrates a method for checking whether the plane of the irradiation field and the incident surface of the FPD 103 are parallel.

In FIG. 5A, the position of the FPD 103 is expressed by the vector $OP_D$, and the center of the irradiation field is expressed by the vector $OP_3$+T×vector e (where T is a positive constant; the endpoint of the vector e is denoted by Q). To calculate a difference between the center of the FPD 103 and that of the irradiation field, $d_{min}$ is calculated as follows:

$$d_{min} = \min_{t \geq 0} |\overrightarrow{OP_D} - (\overrightarrow{OP_3} + t\vec{e})|.$$

Eq. 13

The determination can then be made as follows:

$$\begin{cases} \text{centers match,} & \text{if } 0 \le d_{min} \le T_p \\ \text{centers do not match,} & \text{if } d_{min} > T_p \text{ or no solution,} \end{cases} \quad \text{Inequality 14}$$

where $T_p$ is a threshold indicating the allowable range of distance.

If the coordinates $P_D$ and the vector $P_3Q$ are expressed by equations on three-dimensional coordinates, whether the centers match can be determined by calculating the distance between the point $P_D$ and the half line $P_3Q$ by substitution into a known formula, and comparing the distance with the threshold $T_p$.

The vector e indicates the traveling direction of the radiation emitted from the tube 115. This vector e can be determined from information about the dimensions of the visiting cart 101 and the current orientation of the radiation generation apparatus 102 (the current orientation is measured by the first orientation measurement unit 113). For example, the vector e may be the positional difference between the radiation generation apparatus 102 at position $P_3$ and the diaphragm 116 at position $P_4$.

In FIG. 5B, whether the plane of the irradiation field of radiation and the incident surface of the FPD 103 are parallel is checked by checking whether a normal vector $n_1$ perpendicular to the surface of the radiation generation apparatus 102 from which radiation is emitted and a normal vector n 2 perpendicular to the surface of the FPD 103 where the radiation is incident are in the same and opposite directions. In other words, that the angle formed between the two normal vectors $n_1$ and $n_2$ is near 180° can be checked by calculating cos θ:

$$\cos\theta = \frac{\vec{n_1} \cdot \vec{n_2}}{|\vec{n_1}||\vec{n_2}|}, \qquad \text{Eq. 15}$$

where • represents the scalar product of the two vectors. The determination is then made as follows:

$$\begin{cases} \text{radiation generation apparatus and } FPD \text{ are parallel,} & \text{if } \cos\theta \le -1 + T_A \\ \text{radiation generation apparatus and } FPD \text{ are not parallel,} & \text{otherwise,} \end{cases} \quad \text{Inequality. 16}$$

where $T_A$ is a threshold indicating the allowable range of the angle.

Here, the three angles of the radiation generation apparatus 102 and the three angles of the FPD 103 (the angles about the axes Xs, Ys, and Zs and the angles about the axes $X_D$, $Y_D$, and $Z_D$) are calculated and compared with each other. Whether the plane of the irradiation field of the radiation emitted from the radiation generation apparatus 102 and the incident surface of the FPD 103 are parallel can thereby be checked.

The two normal vectors $n_1$ and $n_2$ can be calculated, for example, by calculating the normal vectors to the two planes in the reference orientation before rotation, and rotating the normal vectors based on angles calculated from the values of various sensors. The vector e used in FIG. 5A may be used as the normal vector $n_1$ to the radiation generation apparatus 102. The normal vectors after rotation can be calculated in a known rotation matrix form.

As described above, the orientation determination unit 209 compares the orientation of the FPD 103 calculated from the values of the first orientation measurement unit 113 with the orientation of the radiation generation apparatus 102 calculated from the values of the second orientation measurement unit 118 based on the foregoing equations. The orientation determination unit 209 determines whether the radiation generation apparatus 102 and the FPD 103 are directly opposed based on the comparison result.

If the relative relationship in orientation is determined to be such that the centers of the radiation generation apparatus 102 and the FPD 103 match and the radiation generation apparatus 102 and the FPD 103 are parallel, the orientation determination unit 209 determines that the two are directly opposed, and notifies the control unit 205 of the determination result. As employed herein, being directly opposed refers not only to a case where the amount of discrepancy in distance in determining the centers and the amount of discrepancy in angle in determining the parallelism are exactly 0, but also covers a case where user-acceptable ranges are set as thresholds for the amounts of discrepancy and both the amounts of discrepancy are less than or equal to the respective thresholds.

Alternatively, whether the two are directly opposed can be determined in a simplified manner by using at least one of a total of six components including the three positional components about the three axes and the three angular components about the three axes. For example, in determining whether the two are directly opposed using only the angles of rotation about two axes except for the rotation about the axis parallel to the gravity, the determination can be made by using only the angles calculated from the values measured by the acceleration sensors. In making the determination about the three axes, the rotation about the axis parallel to the gravity may be calculated from the value measured by an azimuth sensor (magnetic sensor). A distance may be determined by using a value measured using a Bluetooth® or other wireless devices.

Return to the description of FIG. 4. In step 413, if it is found that the centers of the radiation generation apparatus 102 and the FPD 103 match and the radiation generation apparatus 102 and the FPD 103 are parallel as a result of checking the directly opposed relationship therebetween (YES in step 413), the processing proceeds to step 415.

If it is found that the centers of the radiation generation apparatus 102 and the FPD 103 do not match or the radiation generation apparatus 102 and the FPD 103 are not parallel as a result of checking the directly opposed relationship therebetween (NO in step 413), the processing proceeds to step 414. In step 414, the control unit 205 displays a warning without irradiating the FPD 103 with radiation. A warning of the centers not matching and a warning of the two not being parallel can be separately issued to give the user clues for repositioning.

In the present exemplary embodiment, irradiation is not permitted when a warning is displayed. However, irradiation may be permitted while displaying a warning. In such a case, the irradiation may be permitted if an irradiation button is pressed for a specific time or more or if the irradiation button is pressed again after the warning display.

In step 415, the radiation generation apparatus 102 irradiates the FPD 103 with radiation through the object 105 for radiographic imaging. The processing proceeds to step 416.

In step 416, the control unit 205 stops the measurement of the radiation generation apparatus 102 and the FPD 103 at the second sampling period TS by the first and second orientation measurement units 113 and 1182. The control unit 205 then controls the second orientation measurement unit 118 at a sampling period longer than the second sampling period TS2.

Examples of the control at a sampling period longer than the second sampling period TS2 may include controlling the second orientation measurement unit 118 at the first sampling period TS1 or at a sampling period different from the first sampling period TS1. The measurement by the second orientation measurement unit 118 may be ended.

The processing proceeds to step 417.

In step 417, a radiographic image is obtained from the FPD 103 based on the radiation with which the FPD 103 is irradiated in step 415. Information about the orientation of the radiation generation apparatus 102 and the FPD 103 is added to the radiographic image. The orientation information can be added to the radiographic image by the first control apparatus 201 in the visiting cart 101, for example.

The orientation information is added using a common method, such as addition to the image header, embedding into the radiographic image itself (for example, pixel values in a specific area of the image can be reduced to embed numerical values of the orientation into the image), and generation of a dedicated file recording the orientation information. The orientation information to be added includes the angles of the radiation generation apparatus 102 and the FPD 103 and the SID, for example.

The orientation information obtained and added is displayed on the first display device 111 or the second display device 117. For example, the user can examine whether the imaging is successful and, if failed, the cause of the imaging failure (imaging error) based on the image and the orientation information obtained.

The procedure of FIG. 4 illustrating the operation of the radiographic apparatus 100 according to the present exemplary embodiment ends.

Figures 6A, 6B, 6C, 6D:
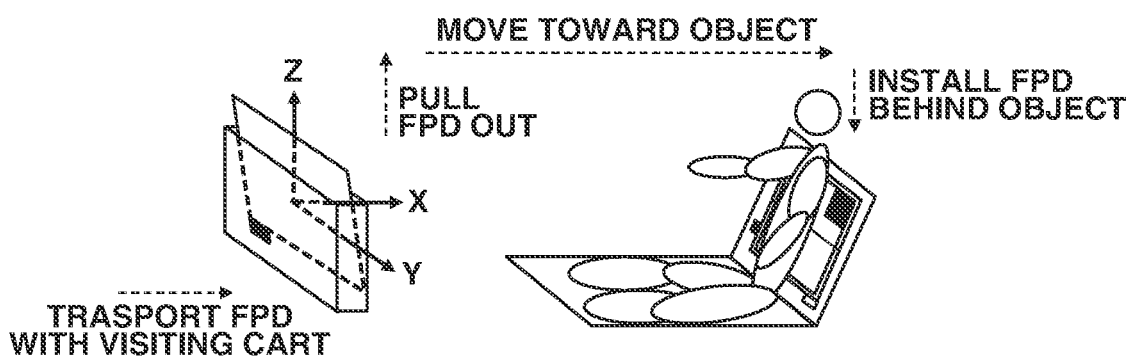
FIGS. 6A to 6D are a diagram illustrating movement of the radiation detector and timing charts illustrating timing to change a sampling period according to the first exemplary embodiment.

FIGS. 6A to 6D are a diagram illustrating movement of the FPD 103 and timing charts illustrating timing to change the sampling periods. FIG. 6A illustrates the FPD 103 accommodated in the FPD accommodation unit 110 of the visiting cart 101 and the object 105 for the FPD 103 to be set for. The motions of pulling out the FPD 103, moving the FPD 103 toward the object 105, and installing the FPD 103 behind the object 105 by the user are illustrated in FIG. 6A. The directions of the X-, Y-, and Z-axes in this diagram are the same as those in FIG. 3A.

In FIG. 6A, the motions of moving the FPD 103 by the user are illustrated by broken-lined arrows. For ease of description, the moving directions will be simplified as follows: The motion of transporting the FPD 103 with the visiting cart 101 is only in the X-axis positive direction. The motion of pulling out the FPD 103 is only in the Z-axis positive direction. The motion of moving the FPD 103 toward the object 105 is only in the X-axis positive direction. The motion of installing the FPD 103 behind the object 105 is only in the Z-axis negative direction.

FIG. 6B illustrates the speed of the FPD 103 in the X-axis direction, calculated from the acceleration in the X-axis direction measured by the second orientation measurement unit 118. FIG. 6C illustrates the speed of the FPD 103 in the Z-axis direction, calculated from the acceleration in the Z-axis direction measured by the second orientation measurement unit 118. FIG. 6D illustrates the sampling period of the second orientation measurement unit 118. In FIGS. 6A to 6D, the movement in the Y-axis direction is omitted for ease of description.

At time t100 in FIGS. 6B to 6D, the speed in the X-axis direction measured by the second orientation measurement unit 118 has a positive value and the speed in the Z-axis direction has a value of zero. In such a case, the visiting cart 101 is determined to be moving, and the second orientation measurement unit 118 continues measurement at the first sampling period TS1. If the speed in the X-axis direction, the speed in the Z-axis direction, and not-illustrated speed in the Y-axis direction measured by the second orientation measurement unit 118 have a value of zero, specifically, the speed of the visiting cart 101 is zero in all directions, the visiting cart 101 can be determined to be stopped.

The motion of taking the FPD 103 out of the FPD accommodation unit 110 is started between times t101 and t102 of FIG. 6D, and ended at time t102. As illustrated in FIGS. 6B and 6C, the speed in the X-axis direction between times t101 and t102 is measured to have a value of zero, and the speed in the Z-axis direction is measured to have a positive value.

The FPD 103 moves toward the object 105 between times t102 and t103. The speed in the X-axis direction is thus measured to have a positive value, and the speed in the Z-axis direction is measured to have a value of zero.

Next, the motion for installing the FPD 103 behind the object 105 is started at time t103 and ended between times t104 and t105. In the meantime, the speed in the X-axis direction is measured to have a value of zero, and the speed in the Z-axis direction is measured to have a negative value.

At time t105, as illustrated in FIGS. 6B and 6C, the speeds in both the X- and Z-axis directions are measured to have a value of zero. If the measurements on all the axes are zero, the movement of the FPD 103 can be determined to be stopped. The control unit 205 thus outputs a completion signal indicating the completion of the positioning, based on the values of the second orientation measurement unit 118. The signal output unit 206 receives the completion signal, and then outputs a trigger signal for switching the sampling periods to a longer one. In response to the trigger signal, the control unit 205 ends the measurement at the second sampling period TS2 by the first and second orientation measurement units 113 and 118.

Although omitted in FIGS. 6A to 6D, the radiation generation apparatus 102 is also desirably moved in positioning. In addition to the FPD 103, the radiation generation apparatus 102 is therefore desirably at rest when the completion signal is output.

It is suitable that the determination at time t101 as to whether the visiting cart 101 carrying the FPD 103 is at rest and the determination at time t105 as to whether the positioning-completed FPD 103 stops moving are made after a lapse of a specific time from when the values on all the axes become zero. The user may be allowed to change the time to make the stop determinations based on the usage. In view of the noise component of the second orientation measurement unit 118, thresholds may be set for the determinations as to whether the values on all the axes are zero, so that up to certain values are regarded as zero.

The signal output unit 206 may output the trigger signal in response to the reception of a stop signal indicating that the visiting cart 101 stops, and the control unit 205 may change the sampling period of the second orientation measurement unit 118 to the second sampling period TS2 in response to the trigger signal.

For example, the visiting cart 101 that has entered a hospital room to round is shortly moved to near an object 105 and stopped. The sampling period may therefore be changed in response to the entry. More specifically, a device for transmitting an entry signal indicating the entry into the hospital room is installed, and when the visiting cart 101 receives the entry signal, the signal output unit 206 outputs the trigger signal and the control unit 205 changes the sampling period of the second orientation measurement unit 118 to the second sampling period TS2.

In the description so far, the timing to end the control and measurement at the second sampling period TS2 is described to come after the timing when the FPD 103 is stopped. However, that the radiation generation apparatus 102 and the FPD 103 are directly opposed may be added as a condition.

For example, the control and measurement at the second sampling period TS2 may be ended at timing when the radiation generation apparatus 102 and the FPD 103 are determined to be directly opposed and the FPD 103 is stopped. The addition of the determination as to whether the radiation generation apparatus 102 and the FPD 103 are directly opposed as a condition prevents the measurement at the second sampling period TS2 from being erroneously ended during positioning.

In the present exemplary embodiment, the first orientation measurement unit 113 does not necessarily need to be a sensor, such as an acceleration sensor, a geomagnetic sensor, and an angular velocity sensor. For example, the first orientation measurement unit 113 may measure the rotation and the extension and contraction of the first and second arms 106 and 107 and the rotation of the diaphragm 116.

For example, a mechanism for controlling the rotation and the extension and contraction can be constituted by using stepping motors, which are known electrical parts, and the first control apparatus 201 of the visiting cart 101. In such a case, the control unit 205 can calculate the orientation from parameters used in such a control mechanism (orientation control parameters) instead of calculating the orientation based on the values measured by a sensor.

In the present exemplary embodiment, a distance is derived using an acceleration sensor. However, a wireless LAN device, a Bluetooth® device, or a UWB device may be used as described above. Alternatively, a position can be identified by deriving a distance using a magnetic sensor in an artificially generated magnetic field. An acceleration sensor and a wireless LAN device, a Bluetooth® device, a UWB device, or a magnetic sensor can be combined to further improve the accuracy of distance measurement.

Similarly, the accuracy of angle measurement can be further improved by combining an angle obtained by a gravity sensor with an angle calculated from an angular velocity or an azimuth angle calculated from the Earth's magnetic field.

In the present exemplary embodiment, the control unit 205, the signal output unit 206, and the reference calculation unit 208 of the first control apparatus 201 may be included into the second control apparatus 203. The orientation determination unit 209 of the second control apparatus 203 may be included into the first control apparatus 201.

In the present exemplary embodiment, the timing for the signal output unit 206 to output the trigger signal is when the reference orientation is set. However, this is not restrictive. It is sufficient that the sampling periods is reduced during the positioning of the radiation generation apparatus 102 and the FPD 103 for radiographic imaging. When the visiting cart 101 is moving, the positioning of the radiation generation apparatus 102 and the FPD 103 is not performed and the sampling periods are therefore desirably long in view of the power consumption of the first and second orientation measurement units 113 and 118.

In the present exemplary embodiment, the signal output unit 206 thus outputs the trigger signal between the reception of the stop signal indicating that the visiting cart 101 carrying the FPD 103 is at rest or stops and the reception of the completion signal indicating the completion of the positioning of the FPD 103 for radiographic imaging. The control unit 205 then controls the second orientation measurement unit 118 to reduce the sampling period of the second orientation measurement unit 118 in response to the reception of the trigger signal. The control unit 205 similarly controls the first orientation measurement unit 113 to reduce the sampling period of the first orientation measurement unit 113 in response to the reception of the trigger signal.

For example, the signal output unit 206 may output the trigger signal in response to input of an imaging protocol of radiographic imaging after the visiting cart 101 carrying the FPD 103 stops (i.e., immediately after the determination of step 403 in FIG. 4).

The signal output unit 206 may output the trigger signal in response to detection of a fact that the visiting cart 101 stops with the FPD 103 accommodated in the FPD accommodation unit 110 (i.e., immediately after the determination of step 407 in FIG. 4).

In the present exemplary embodiment, the power consumption can be reduced by restoring the sampling periods to the first sampling period TS1 or ending the measurement immediately after a situation where accurate measurement at the second sampling period TS2 is desirable ends.

For example, the control unit 205 outputs the completion signal indicating the completion of the positioning based on the values measured by the first and second orientation measurement units 113 and 118. The signal output unit 206 outputs the trigger signal in response to the completion signal, and the control unit 205 controls the sampling periods of the first and second orientation measurement units 113 and 118 to be longer than the second sampling period TS2 in response to the trigger signal.

The completion signal indicating the completion of the positioning is not limited to the foregoing example, and various signals occurring after the completion of the positioning may be used. For example, a signal for starting radiographic imaging may be used as the completion signal. Specific examples include a signal occurring when an irradiation switch for instructing the visiting cart 101 to emit radiation from the tube 115 is pressed. If the FPD 103 has a function of detecting radiation irradiation, a signal occurring in response to the detection may be used as the completion signal.

By the way, the visiting cart 101 may stop during transportation, such as when waiting for an elevator. If the sampling periods are switched to the shorter second sampling period TS2 in response to such a halt during transportation, the power consumption of the first and second orientation measurement units 113 and 118 increases since the sampling periods become shorter in a situation where accurate measurement is not needed.

The control unit 205 then controls the sampling period back to the first sampling period TS1 if the positioning of the FPD 103 for radiographic imaging is not started within a predetermined time when the second orientation measurement unit 118 is performing measurement at the shorter second sampling period TS2. The control unit 205 may similarly control the radiation generation apparatus 102. The control unit 205 controls the sampling period of the first orientation measurement unit 113 back to the first sampling period TS1 if the positioning of the radiation generation apparatus 102 for radiographic imaging is not started within a predetermined time.

If, for example, the visiting cart 101 has brakes, the sampling periods may be switched based on a signal for detecting the application of the brakes.

More specifically, the brakes are often unused when the visiting cart 101 stops during transportation. The control unit 205 thus controls the sampling periods to not be switched to the second sampling period TS2 if the brakes are not used. When the visiting cart 101 is moved to near the object 105 to start the positioning of the radiation generation apparatus 102 and the FPD 103, the position of the visiting cart 101 is fixed using the brakes. The control unit 205 may thus control the switching of the sampling periods to the second sampling period TS2 when the brakes are used.

In positioning the radiation generation apparatus 102 and the FPD 103 through the foregoing method, the first and second orientation measurement units 113 and 118 perform measurement at the shorter second sampling period TS2 so that measurement accuracy improves. In other periods, the first and second orientation measurement units 113 and 118 perform measurement at the longer first sampling period TS1, so that the power consumption can be reduced.

The positional relationship between the radiation generation apparatus 102 and the FPD 103 can thus be accurately calculated while reducing the power consumption of the radiation generation apparatus 102 and the FPD 103 having the first and second orientation measurement units 113 and 118 built-in, respectively.

In a second exemplary embodiment, a method for further reducing the power consumption as compared with the first exemplary embodiment, with the period where measurement is performed at the shorter second sampling period TS2 minimized will be described.

A radiographic apparatus according to the present exemplary embodiment has a configuration similar to that of the first exemplary embodiment. A description thereof will thus be omitted. The operation flowchart of FIG. 7 and the diagram illustrating the movement of the FPD 103 and the timing charts of FIGS. 8A to 8D have similarities with FIG. 4 and FIGS. 6A to 6D, respectively. A description thereof will therefore also be omitted.

Figure 7:
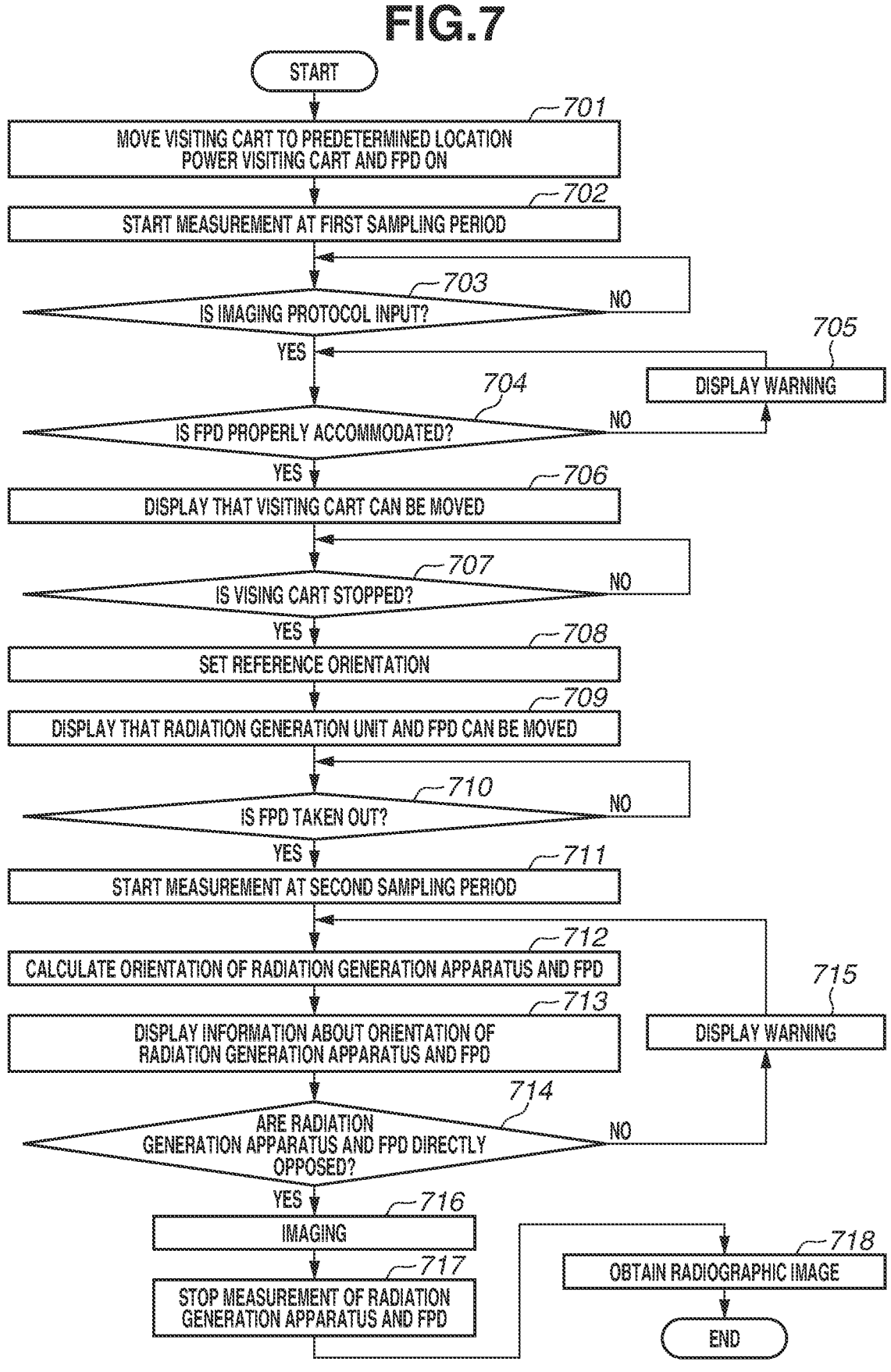
FIG. 7 is a flowchart illustrating an operation of a radiographic apparatus according to a second exemplary embodiment.
Figures 8A, 8B, 8C, 8D:
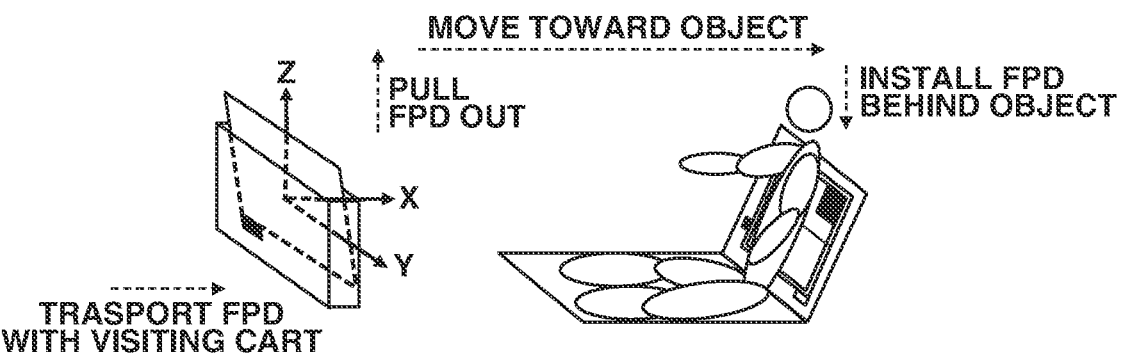
FIGS. 8A to 8D are a diagram illustrating movement of a radiation detector and timing charts illustrating timing to change a sampling period according to the second exemplary embodiment.

FIG. 7 illustrates an operation procedure of the radiographic apparatus 100 according to the second exemplary embodiment. A difference from the operation procedure of FIG. 4 is that the timing for the control unit 205 to switch the sampling periods of the first and second orientation measurement units 113 and 118 to the second sampling period TS2 is immediately after the FPD 103 is taken out of the FPD accommodation unit 110.

FIGS. 8A to 8D are the diagram illustrating the movement of the FPD 103 and the timing charts illustrating the timing when the control unit 205 changes the sampling periods. In FIGS. 8A to 8D, the control unit 205 switches the sampling periods to the second sampling period TS2 at time t202. Time t202 refers to the moment when the speed in the X-axis direction measured by the second orientation measurement unit 118 has a value of zero and the speed in the Z-axis direction changes from zero.

In other words, in the present exemplary embodiment, the signal output unit 206 outputs the trigger signal based on the determination that the FPD 103 is taken out of the FPD accommodation unit 110.

In the foregoing description, the control unit 205 makes the determination that the FPD 103 has been taken out of the FPD accommodation unit 110 based on the change in the speed in the Z-axis direction from zero. However, this is not restrictive. For example, a threshold may be set in view of the noise component of the second orientation measurement unit 118, and speed lower than or equal to the threshold may be determined to be halt.

The control unit 205 may set a threshold for the position of the FPD 103, and determine that the FPD 103 is taken out of the FPD accommodation unit 110 if the position of the FPD 103 changes by more than or equal to the threshold based on converted position information obtained from the acceleration sensor in the second orientation measurement unit 118. For example, the control unit 205 may determine that the FPD 103 is taken out of the FPD accommodation unit 110 based on movement of the FPD 103 as much as the amount of connector insertion in the Z-axis positive direction of FIG. 6A. The control unit 205 may similarly determine that the FPD 103 is taken out of the FPD accommodation unit 110 based on movement of the FPD 103 as much as the depth of the pocket in the FPD accommodation unit 110 in the Z-axis positive direction of FIG. 6A.

The control unit 205 may measure the movement of the FPD 103 as described above to determine whether the FPD 103 is taken out of the FPD accommodation unit 110, but this is not restrictive.

For example, the FPD accommodation unit 110 may include a connector of the first accommodation determination device 112, and the determination may be made based on the detection of electrical disconnection of the first and second accommodation determination devices 112 and 114. If the connector is electrically connected to the battery 150 or an external power supply, the FPD 103 can be powered by the first and second accommodation determination devices 112 and 114 being connected. In such a case, the determination may be made based on detection of electrical disconnection of the FPD 103 from the battery 150 or the external power supply.

While in FIGS. 8A to 8D the signal output unit 206 is described to output the trigger signal in response to detection of the movement of the FPD 103, the first orientation measurement unit 113 may detect the positioning movement of the radiation generation apparatus 102 and the signal output unit 206 may output the trigger signal.

Such a method enables minimization of the period where measurement is performed at the second sampling period TS2 as compared with the case where the measurement at the second sampling period TS2 is started immediately after the setting of the reference orientation, as in the first exemplary embodiment. The power consumption of the first and second orientation measurement units 113 and 118 can thus be reduced.

A third exemplary embodiment describes a method for changing the sampling periods at user-intended timing. A radiographic apparatus according to the present exemplary embodiment has a configuration similar to that of the first exemplary embodiment. A description thereof will thus be omitted.

In the present exemplary embodiment, the sampling periods of the first and second orientation measurement units 113 and 118 are changed with a user operation on the switch 130 as a trigger. Here, the sampling periods are switched from the first sampling period TS1 to the second sampling period TS2 shorter than the first sampling period TS1. In such a manner, the sampling periods can be changed at the user-intended timing. The sampling periods may be switched to the first sampling period TS1 if the switch 130 is operated when the second sampling period TS2 is set.

In the present exemplary embodiment, the switch 130 is described to be included in the FPD 103 as illustrated in FIGS. 1A and 1B. However, the switch 130 may be included in the visiting cart 101.

Such a method enables switching of the sampling periods of the first and second orientation measurement units 113 and 118 based on the user's instructions, thus realizing measurement of the orientation with high accuracy. In addition, the power consumption of the first and second orientation measurement units 113 and 118 can be reduced.

All the foregoing exemplary embodiments of the present invention are just specific examples of implementation of the present invention, and the technical scope of the present invention is not limited in its interpretation to the foregoing. In other words, the present invention can be implemented in various forms without departing from the technical concept or main features thereof.

The present invention is not limited to the foregoing exemplary embodiments, and various changes and modifications can be made without departing from the spirit and scope of the present invention. The following claims are therefore attached to make the scope of the present invention public.

According to an exemplary embodiment of the present invention, the positional relationship between a radiation generation apparatus and a radiation detector can be accurately calculated while reducing the power consumption of acceleration sensors included in the radiation generation apparatus and the radiation detector.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiographic system comprising:
a radiation detector configured to perform radiographic imaging;
a visiting cart configured to removably accommodate the radiation detector;
a radiation generation apparatus mounted on the visiting cart;
a first orientation measurement unit configured to perform measurement of orientation of the radiation detector;
a signal output unit configured to output a trigger signal after receiving a stop signal indicating that a visiting cart carrying the radiation detector is at rest or stops but before receiving a completion signal indicating completion of positioning between the radiation detector, which has been taken out of the visiting cart, and the radiation generation apparatus; and
a control unit configured to control the first orientation measurement unit to shorten a sampling period of the measurement upon receiving the trigger signal.

2. The radiographic system according to claim 1, wherein the control unit is configured to, in a case where speed of the visiting cart calculated based on a value measured by the first orientation measurement unit falls to or below a predetermined threshold, output the stop signal.

3. The radiographic system according to claim 1,
further comprising a second orientation measurement unit different from the first orientation measurement unit and configured to perform measurement of orientation of the radiation generation apparatus, and
wherein the control unit is configured to control the second orientation measurement unit to shorten a sampling period of the measurement of the orientation of the radiation generation apparatus based on the reception of the trigger signal.

4. The radiographic system according to claim 1,
wherein the visiting cart includes an accommodation unit configured to accommodate the radiation detector to carry the radiation detector, and
wherein the signal output unit is configured to perform detection of the stop signal of the visiting cart with the radiation detector accommodated in the accommodation unit, and output the trigger signal based on the detection.

5. The radiographic system according to claim 1,
wherein the visiting cart includes an accommodation unit configured to accommodate the radiation detector to carry the radiation detector, and
wherein the signal output unit is configured to make a determination as to whether the radiation detector has been taken out of the accommodation unit, and output the trigger signal based on the determination.

6. The radiographic system according to claim 1, further comprising a switch configured to receive a user's operation, wherein the signal output unit is configured to output the trigger signal based on the operation.

7. The radiographic system according to claim 1, wherein the signal output unit is configured to output the trigger signal based on an input of an imaging protocol of the radiographic imaging by the radiographic system from an input unit included in the radiographic system.

8. The radiographic system according to claim 1, wherein the first orientation measurement unit is an angular velocity sensor or an acceleration sensor.

9. The radiographic system according to claim 1, wherein the radiation detector includes a battery.

10. The radiographic system according to claim 1, wherein the visiting cart includes a battery configured to supply power to the radiation detector.

11. The radiographic system according to claim 3, wherein the control unit is configured to control the first orientation measurement unit and the second orientation measurement unit to perform respective measurements at a second sampling period that is shorter than a first sampling period, based on the reception of the trigger signal.

12. The radiographic system according to claim 3, wherein the second orientation measurement unit is an angular velocity sensor or an acceleration sensor.

13. The radiographic system according to claim 11, further comprising an orientation determination unit configured determine whether the radiation detector and the radiation generation apparatus are directly opposed, based on a relative relationship in orientation between the radiation detector and the radiation generation apparatus obtained from values of the first and second orientation measurement units.

14. The radiographic system according to claim 13, wherein the orientation determination unit is configured to make the determination by comparing the orientation of the radiation detector calculated from the value of the first orientation measurement unit and the orientation of the radiation generation apparatus calculated from the value of the second orientation measurement unit.

15. The radiographic system according to claim 5,
wherein the accommodation unit includes a power supply unit configured to be connected to the radiation detector to supply power to the radiation detector, and
wherein the signal output unit is configured to perform detection of disconnection of the radiation detector from the power supply unit, and output the trigger signal based on the detection.

16. A radiation detector for use in a radiographic system including a radiation generation apparatus and a visiting cart configured to carry both the radiation detector and the radiation generation apparatus:
a radiation detection unit configured to perform radiographic imaging;
an orientation measurement unit configured to perform measurement of orientation of the radiation detector;
a signal output unit configured to output a trigger signal after receiving a stop signal indicating that the visiting cart is at rest or stops but before receiving a completion signal indicating completion of positioning between the radiation detector, which has been taken out of the visiting cart, and the radiation generation apparatus; and
a control unit configured to control the orientation measurement unit to shorten a sampling period of the measurement upon receiving the trigger signal.

17. A control apparatus of a radiographic system, the radiographic system including a radiation generation apparatus, a radiation detector configured to perform radiographic imaging and an orientation measurement unit configured to perform measurement of orientation of the radiation detector, and a visiting cart configured to carry both the radiation detector and the radiation generation apparatus, the control apparatus comprising:
a signal output unit configured to output a trigger signal after receiving a stop signal indicating that the visiting cart is at rest or stops but before receiving a completion signal indicating completion of positioning between the radiation detector, which has been taken out of the visiting cart, and the radiation generation apparatus; and
a control unit configured to control the orientation measurement unit to shorten a sampling period of the measurement upon receiving the trigger signal.

18. A method for controlling a radiographic system, the radiographic system including a radiation generation apparatus, a radiation detector configured to perform radiographic imaging and an orientation measurement unit configured to perform measurement of orientation of the radiation detector, and a visiting cart configured to carry both the radiation detector and the radiation generation apparatus, the method comprising:
outputting a trigger signal after receiving a stop signal indicating that the visiting cart is at rest or stops but before receiving a completion signal indicating completion of positioning between the radiation detector, which has been taken out of the visiting cart, and the radiation generation apparatus; and
controlling the orientation measurement unit to shorten a sampling period of the measurement upon receiving the trigger signal.

19. A non-transitory computer-readable storage medium storing a program for causing a computer to execute the control method according to claim 18.

* * * * *